(12) United States Patent
Decré et al.

(10) Patent No.: US 9,242,086 B2
(45) Date of Patent: Jan. 26, 2016

(54) SYSTEM FOR MEDICAL STIMULATION COMPRISING A PROBE

(75) Inventors: Michel Marcel Jose Decré, Eindhoven (NL); Michel Gerardus Pardoel, Eindhoven (NL)

(73) Assignee: MEDTRONIC BAKKEN RESEARCH CENTER B.V., Maastricht (NL)

( * ) Notice: Subject to any disclaimer, the term of this patent is extended or adjusted under 35 U.S.C. 154(b) by 0 days.

(21) Appl. No.: 13/574,803

(22) PCT Filed: Jan. 20, 2011

(86) PCT No.: PCT/IB2011/050254
§ 371 (c)(1), (2), (4) Date: Jul. 24, 2012

(87) PCT Pub. No.: WO2011/092614
PCT Pub. Date: Aug. 4, 2011

(65) Prior Publication Data
US 2012/0303107 A1    Nov. 29, 2012

(30) Foreign Application Priority Data
Jan. 27, 2010 (EP) ..................... 10151779

(51) Int. Cl.
*A61N 1/05* (2006.01)
*A61M 25/01* (2006.01)

(52) U.S. Cl.
CPC .............. *A61N 1/05* (2013.01); *A61M 25/0102* (2013.01); *A61N 1/0551* (2013.01)

(58) Field of Classification Search
CPC ... A61N 1/36082; A61N 1/05; A61N 1/0529; A61N 1/056; A61N 1/0534; A61N 1/0539; A61N 1/0531
USPC .......... 607/115, 116, 117, 123, 125, 126, 127
See application file for complete search history.

(56) References Cited

U.S. PATENT DOCUMENTS

| 4,332,259 A | * | 6/1982 | McCorkle, Jr. ............... 607/123 |
| 4,559,951 A | * | 12/1985 | Dahl et al. .................... 600/374 |
| 5,405,374 A |   | 4/1995 | Stein |

(Continued)

FOREIGN PATENT DOCUMENTS

WO    8304181 A1    12/1983

OTHER PUBLICATIONS

International Search Report for International Application No. PCT/IB2011/050254 dated Apr. 28, 2011.

*Primary Examiner* — Christopher D Koharski
*Assistant Examiner* — Pamela M Bays
(74) *Attorney, Agent, or Firm* — Shumaker & Sieffert, P.A.

(57) ABSTRACT

The invention relates a system (302) for medical stimulation. The system (302) comprises an implantable probe (304) bifurcated into a primary branch (306) and a secondary branch (308) at a bifurcation (310), wherein the probe is provided at its distal end (112, 312) with an electrode (114) for delivering electrical stimulation to tissue. Herein, the primary branch (306) is configured for at least temporarily mechanically co-operating with a guide wire (316) configured for guiding the probe (304) into said tissue whereas the secondary branch (308) is configured for electrically connecting said electrode to a device for generating the electrical stimulation.

13 Claims, 5 Drawing Sheets

(56) References Cited

U.S. PATENT DOCUMENTS

Figure 1:
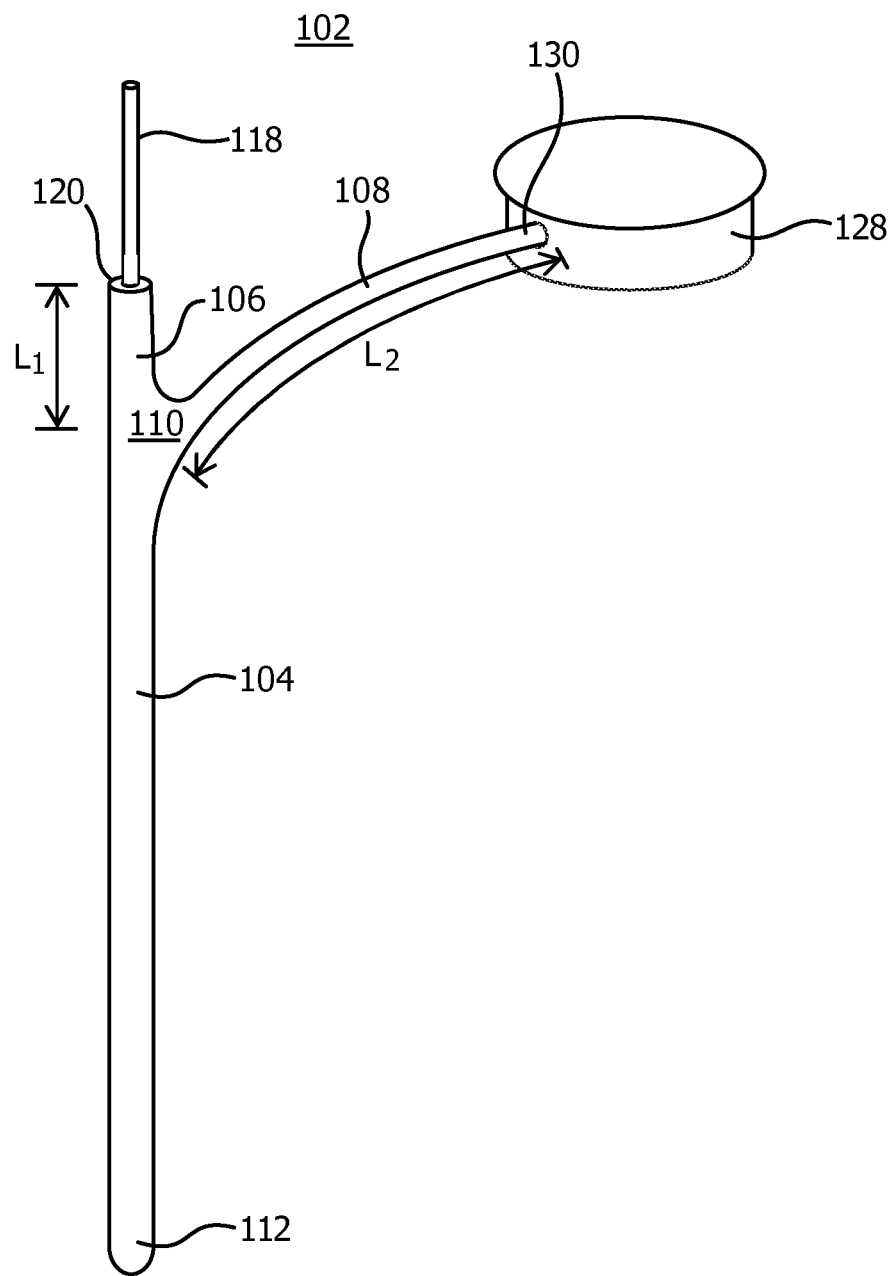

| | | | |
|---|---|---|---|
| 6,889,091 B2 * | 5/2005 | Hine et al. | 607/119 |
| 7,047,082 B1 * | 5/2006 | Schrom et al. | 607/116 |
| 2007/0135861 A1 * | 6/2007 | Wallace et al. | 607/45 |
| 2008/0208306 A1 * | 8/2008 | Rutten | 607/127 |

* cited by examiner

SYSTEM FOR MEDICAL STIMULATION COMPRISING A PROBE

CROSS-REFERENCE TO RELATED APPLICATIONS

This application is a U.S. National Stage of International Patent Application No. PCT/IB2011/050254 filed on Jan. 20, 2011, which claims priority to European Patent Application No. 10151779.5 filed on Jan. 27, 2010, both of which are incorporated herein by reference in their entirety.

FIELD OF THE INVENTION

The invention relates to a system for medical stimulation.

BACKGROUND OF THE INVENTION

Systems for neurostimulation have been used over the past ten years to treat acute or chronic neurological conditions. Such systems comprise a probe having a cylindrically shaped geometry and provided with an electrode situated in the distal end of the probe for delivering electrical pulses to a target tissue. The electrical pulses are generated by a pulse generator not situated in the probe. Therefore an electrical connection extending from the proximal end of the probe is to be established between the electrode and the pulse generator. The probe is guided into the target tissue using a guide wire fitting into the probe and thereby temporarily providing mechanical stiffness to said probe.

A problem of the aforementioned method is that the receiving of the guide wire by the probe complicates the electrical connection extending from the probe to be established before implanting the probe, i.e. before removing the guide wire from the probe, thereby impeding the application of a pre-manufactured electrical connection.

SUMMARY OF THE INVENTION

It is an object of the invention to provide a probe comprising an electrode for delivering medical stimulation and arranged for mechanical co-operation with a guide wire, while allowing for electrically connecting the electrode situated in the probe to a device for generating the medical stimulation before implanting the probe.

This object is achieved by the system according to the invention, which system comprises an implantable probe bifurcated into a primary branch and a secondary branch at a bifurcation, wherein the probe is provided at its distal end with an electrode for delivering electrical stimulation to tissue, wherein the primary branch is configured for at least temporarily mechanically co-operating with a guide wire configured for guiding the probe into said tissue, and wherein the secondary branch is configured for electrically connecting said electrode to a device for generating the electrical stimulation.

The bifurcation of the probe into a primary branch and a secondary branch, wherein the primary branch is arranged for at least temporarily mechanically co-operating with a guide wire and wherein the secondary branch is configured for mutually electrically connecting the electrode and a pulse generator, a spatial separation is effectuated between otherwise spatially conflicting functionalities of the probe. That is, the mechanical co-operation with the guide wire, which co-operation is to provide temporary mechanical resistance against buckling and bending, is spatially separated from any arrangements for electrically connecting the electrode and the pulse generator. Therefore, the co-operation between the probe and the guide wire is not impeded by any arrangement for electrically connecting the electrode to the device which is configured for generating the medical stimulation.

In this text buckling implies the sudden inability of a structural member, e.g. a probe, to withstand a compressive load as a result of the compressive load exceeding some critical level.

In this text, temporarily mechanically co-operating with a guide wire implies mechanical interaction with the guide wire on a temporary basis, e.g. by being removably attached to the guide wire or by releasably accommodating said guide wire.

As aforementioned, by having the secondary branch configured for mutually electrically connecting the electrode and the device for generating the medical stimulation, the system according to the invention advantageously avoids the need of establishing an electrical connection afterwards, i.e. after implementing the probe into a skull. The latter quality will prove particularly advantageous if the size of electrodes decreases and the number of electrodes accordingly increases as to provide more accurate stimulation of a target tissue.

Because the primary branch is configured for mechanically-co-operating with a guide wire as to provide sufficient mechanical stiffness for accurately guiding the probe into the tissue, the system according to the invention advantageously allows the probe to have significantly small mechanical resistance against bending and buckling as to conform to the tissue's geometry thereby preventing the tissue from being damaged after the guide wire's removal.

The bifurcation is mechanically well defined and allows for reinforcing in order to prevent from accidental rupture of either branch from the probe.

The probe may be manufactured from a polymer employing methods known per se, e.g. casting or injection molding of the polymer in an appropriate mold.

In a preferred embodiment of the system according to the invention, the primary branch is provided at its proximal end with an aperture for receiving the guide wire in a canal configured for accommodating said guide wire. This embodiment has the advantage that it prevents the tissue from being damaged by the possibly sharply contoured guide wire.

In a further preferred embodiment of the system according to the invention, the canal extends into the probe beyond the bifurcation. This embodiment advantageously reduces the damage potentially caused by the probe to the tissue after being implanted in said tissue since the mechanical stiffness of the probe is reduced, whereas it simultaneously increases the maneuverability of the probe by a guide wire for the purpose of accurately implanting the probe.

In a further preferred embodiment of the system according to the invention, the system comprises an electrical wire spiraling around the canal for mutually electrically connecting the electrode and the device for generating the medical stimulation. This embodiment is advantageous in that it effectively enables the integration of a relatively flat hence relatively wide electrical wire into the probe that generally has no such flat or wide geometry.

In a further preferred embodiment of the system according to the invention, the canal is closable. This embodiment advantageously prevents bodily fluids or infectious microorganisms from entering the probe. It is to be noted that the process of closing the primary branch is largely facilitated by the branched geometry of the probe as the electrical connection between the electrode and the pulse generator does not interfere with the primary branch.

In a further preferred embodiment of the system according to the invention, the canal is closable by a blocking material injectable into the aperture. This embodiment is advantageous in that it minimizes forces exerted on the primary branch during the process of closing the aperture, thereby avoiding presumable damage of the tissue in which the probe is implantable.

In a practical embodiment of the system according to the invention, the canal is closable by a plug installable in the aperture.

In a further preferred embodiment of the system according to the invention, the primary branch is configured for being ligatured for closing the aperture. This embodiment advantageously allows for easily re-opening the canal, which re-opening may be necessary in case of malfunctioning if any.

In a further preferred embodiment of the system according to the invention, a distance between a proximal end of the secondary branch and the bifurcation is substantially larger than a distance between the proximal end of the primary branch and said bifurcation. This embodiment has the advantage of enabling optimal placement for both the probe and the box as the secondary branch has sufficient length available for implanting the box at any desired position with respect to the probe.

In a further practical embodiment of the system according to the invention, the device for generating the medical stimulation is installable in an implantable box.

In a further preferred embodiment of the system according to the invention, the box comprises an electrical connector for releasably electrically co-operating with a further electrical connector situated at the proximal end of the secondary branch. This embodiment has the advantage of increasing the surgical maneuverability of the probe as the implantable box may be attached and implanted afterwards.

SHORT DESCRIPTION OF THE FIGURES

FIG. 1 schematically displays a three-dimensional image of an embodiment of the system according to the invention.

Figure 2:
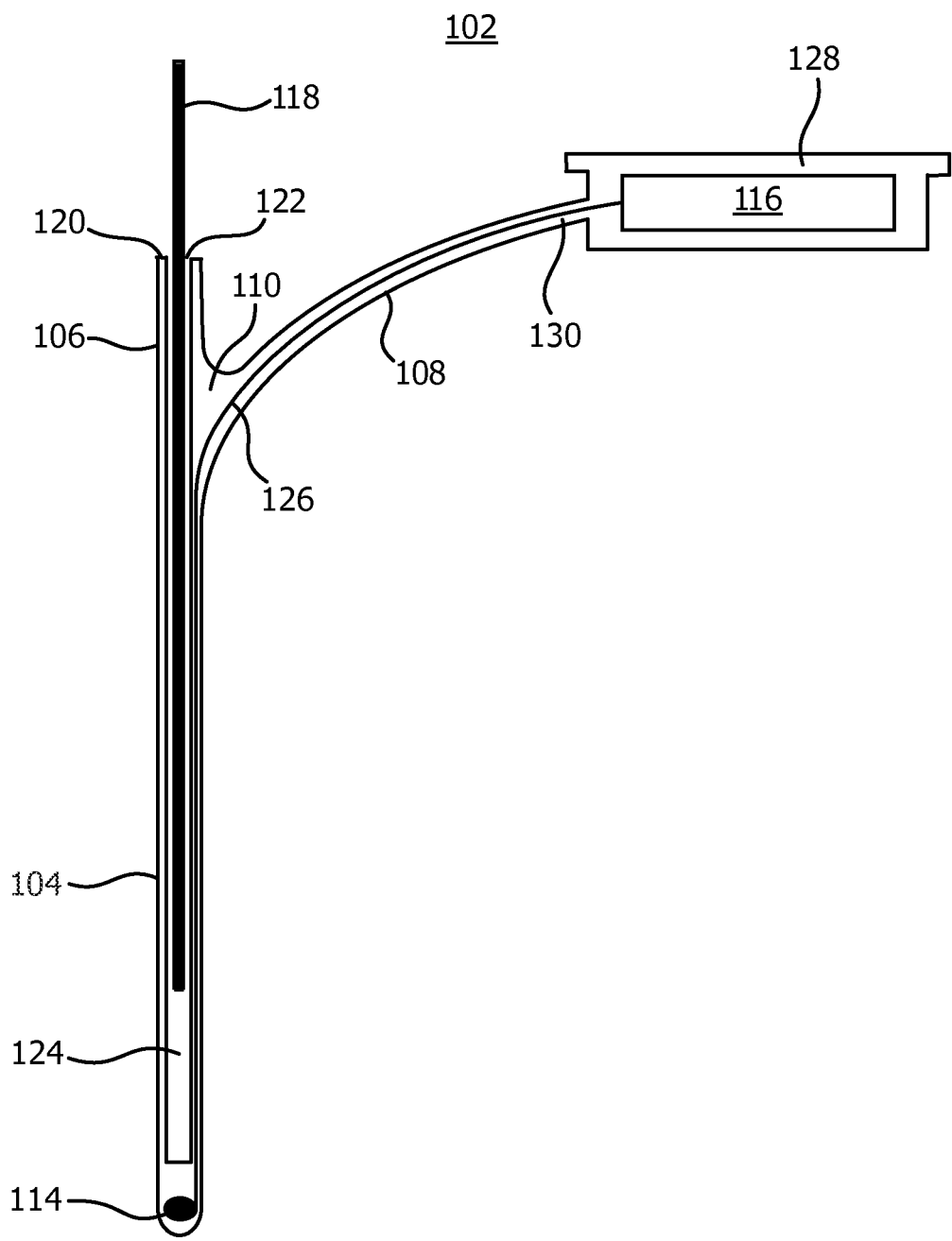

FIG. 2 schematically depicts a cross-sectional image of the embodiment depicted in FIG. 1.

Figure 3:
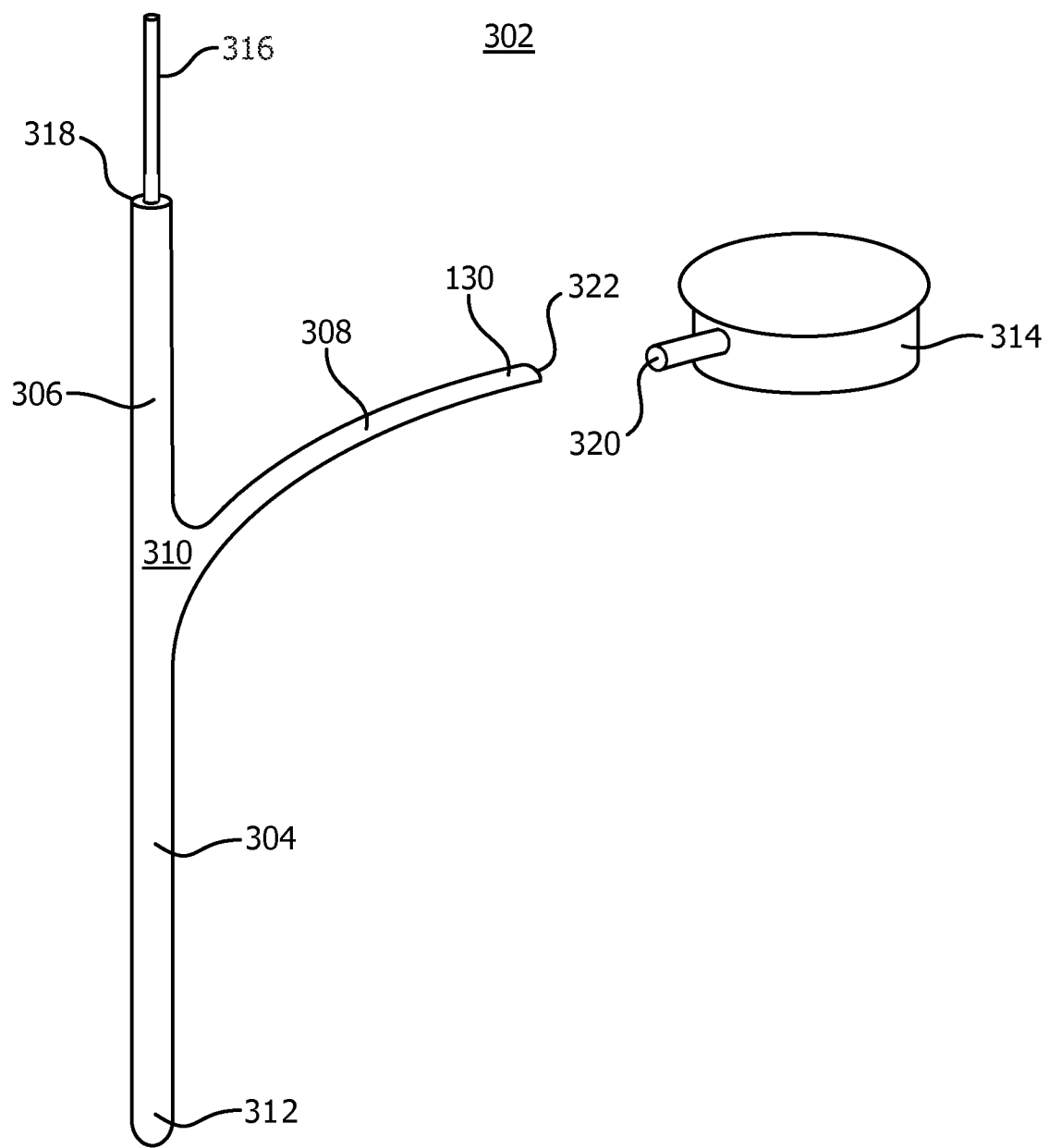

FIG. 3 schematically shows a three-dimensional image of an embodiment of the system according to the invention wherein the primary branch is provided with a canal for temporarily accommodating a guide wire.

Figure 4:
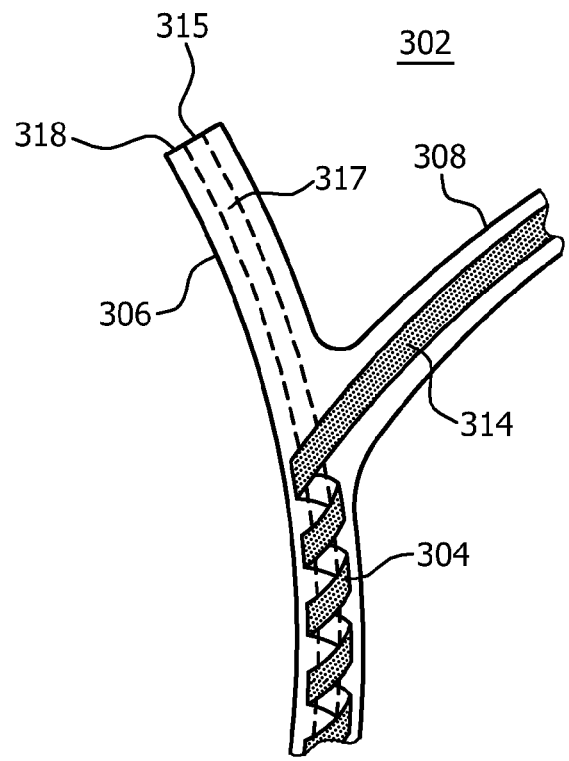

FIG. 4 schematically depicts an electrical wire spiraling around the canal of the probe depicted in FIG. 3.

Figure 5:
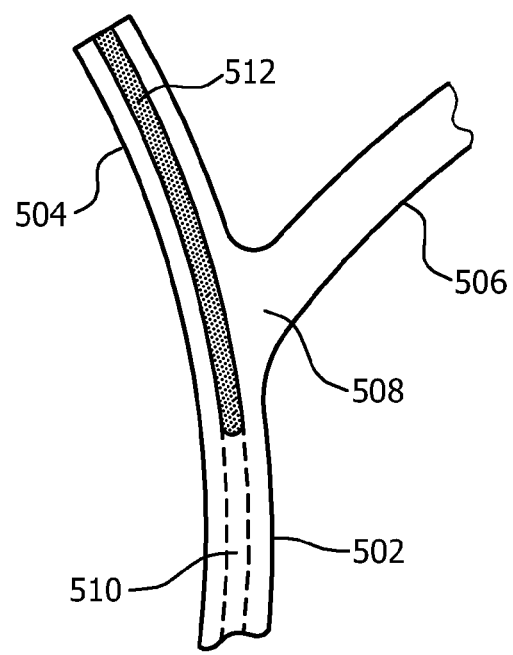

FIG. 5 schematically shows a probe provided with a canal closable by a blocking material.

Figure 6:
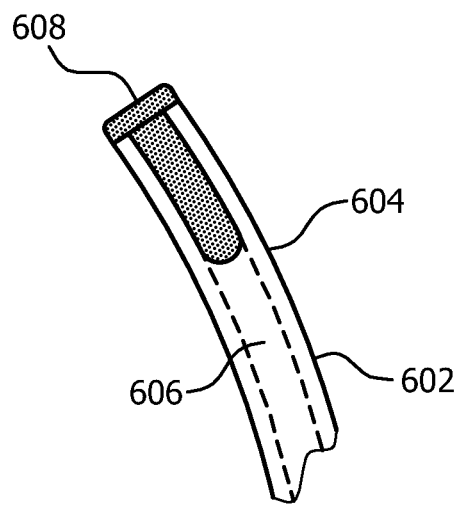

FIG. 6 schematically depicts a probe having a canal closable by a plug.

Figure 7:
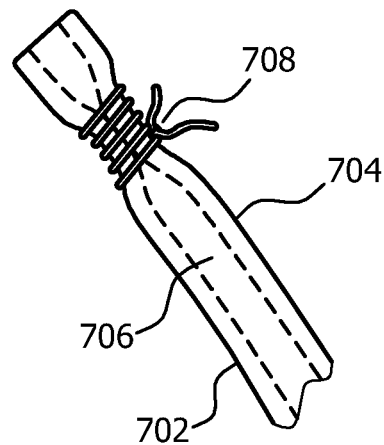

FIG. 7 schematically displays a probe wherein its primary branch is configured for being ligatured as to close the canal situated in the probe.

DETAILED DESCRIPTION OF THE EMBODIMENTS

FIG. 1 schematically displays a system 102 for medical stimulation of a tissue for the therapy of acute or chronic neurological conditions in e.g. the brain or the spine. The system 102 comprises an implantable probe 104 which is bifurcated into a primary branch 106 and a secondary branch 108 at a bifurcation 110. The probe is manufactured from polymers known per se e.g. silicone. Referring to FIG. 2, the probe 104 comprises at its distal end 112 an electrode 114 for delivering medical stimulation, which medical stimulation is generated during operational conditions by a device 116, which device 116 is optionally comprised in the system 102. The medical stimulation for instance encompasses a series of electrical pulses. For the purpose of generating electrical pulses, the device 116 comprises a pulse generator. Referring to FIG. 1, the primary branch 104 is configured for temporarily co-operating with a guide wire 118. Referring to FIG. 2 once more, in this particular embodiment the primary branch 106 is provided at its proximal end 120 with an aperture 122 for the purpose of receiving the guide wire 118 in a canal 124, which canal 124 is configured for at least temporarily accommodating the guide wire 118. In this particular example, the canal 124 extends into the probe 104 beyond the bifurcation point 110. The secondary branch 108 is configured for electrically connecting the electrode 114 to the device 116 for generating the medical stimulation, e.g. via an electrical wire 126. The electrical wire 126 is not restricted to the geometry displayed in FIG. 1; the electrical wire 126 may for instance be integrated into the probe 104 by way of a geometry spiraling around the canal 124. In this particular embodiment, the device 116 is installable in an implantable box 128, which box 128 may be attached to a proximal end 130 of the secondary branch 108. Alternatively, the box 128 may be provided with an electrical connector (not depicted) for releasably co-operating with a further electrical connector (not depicted) situated at the proximal end 130 of the secondary branch 108. In this specific example the distance $L_2$ between the proximal end 130 of the secondary branch 108 and the bifurcation 110, is significantly larger than the distance $L_1$ between the proximal end 120 of the primary branch 106 and said bifurcation 110.

FIG. 3 schematically depicts a system 302 for medical stimulation of tissue. The system 302 comprises an implantable probe 304 which is bifurcated into a primary branch 306 and a secondary branch 308 at a bifurcation 310. The probe 304 comprises at its distal end 312 an electrode (not shown) for delivering said medical stimulation to the tissue e.g. by way of electrical pulses. The medical stimulation is generated during operational conditions by a device (not shown) known per se and optionally comprised in the system 302. Said device is facultatively situated in an implantable box 314. The primary branch 304 is configured for temporarily co-operating with a guide wire 316. In this particular embodiment the primary branch 306 is provided at its proximal end 318 with an aperture 315 for the purpose of receiving the guide wire 316 in a canal 317, see FIG. 4, which canal 317 is configured for at least temporarily accommodating the guide wire 316. The canal optionally extends into the probe 304 beyond the bifurcation point 310. Referring to FIG. 3, the secondary branch 308 is configured for electrically connecting the electrode and the device optionally comprised in the system 302. Herein, for the purpose of releasably electrically connecting the electrode to the device situated in the box 314, the box 314 is provided with an electrical connector 320 configured for releasably co-operating with a further electrical connector (not shown) situated at a proximal end 322 of the secondary branch 308. Referring to FIG. 4, the secondary branch 308 accommodates an electrical wire 324 for electrically connecting the electrode to the further electrical connector. The electrical wire 324 is incorporated in the probe 304 in a geometry spiraling around the canal 317.

FIG. 5 schematically depicts a probe 502 bifurcated in a primary branch 504 and a secondary branch 506 at a bifurcation 508, wherein the primary branch 504 is provided with a canal 510 for temporarily accommodating a guide wire (not shown). The canal 510 is closable by way of a blocking material 512 which is injectable into the canal 510. The blocking material 512 may be manufactured from e.g. silicone or biocompatible glue. Referring to FIGS. 1 and 3, the canals 124 and 317 allow for similar closure, respectively.

FIG. 6 schematically depicts a probe 602 bifurcated in a primary branch 604 and a secondary branch (not shown), wherein the primary branch 604 is provided with a canal 606 for at least temporarily mechanically co-operating with a guide wire (not shown). The canal 606 is closable by way of a plug 608 installable in the canal 606. Referring to FIGS. 1 and 3, the canals 124 and 317 allow for similar closure, respectively.

FIG. 7 schematically depicts a probe 702 bifurcated in a primary branch 704 and a secondary branch (not shown), wherein the primary branch 704 is provided with a canal 706 for at least temporarily accommodating a guide wire (not shown). The canal 706 is configured for being ligatured e.g. by way of a surgical thread 708. Referring to FIGS. 1 and 3, the canals 124 and 317 allow for similar closure, respectively.

While the invention has been illustrated and described in detail in the drawings and in the foregoing description, the illustrations and the description are to be considered illustrative or exemplary and not restrictive. The invention is not limited to the disclosed embodiments. It is noted that the system according to the invention and all its components can be made by applying processes and materials known per se. In the set of claims and the description the word "comprising" does not exclude other elements and the indefinite article "a" or "an" does not exclude a plurality. Any reference signs in the claims should not be construed as limiting the scope. It is further noted that all possible combinations of features as defined in the set of claims are part of the invention.

The invention claimed is:

1. A system for medical stimulation, the system comprising:
   an implantable probe bifurcated into a primary branch and a secondary branch at a bifurcation, the probe including at least one electrode proximate a distal end of the probe for delivering electrical stimulation to brain tissue and an electrical wire for electrically connecting the at least one electrode to a device for generating the electrical stimulation,
   wherein the primary branch is configured for temporarily mechanically co-operating with a guide wire configured for guiding the probe into said brain tissue, the guide wire configured to fit into the probe and temporarily provide mechanical stiffness to the probe,
   wherein the primary branch is provided at its proximal end with an aperture for receiving the guide wire in a canal configured for accommodating the guide wire,
   wherein the secondary branch is configured for electrically connecting said at least one electrode to the device for generating the electrical stimulation, and
   wherein the electrical wire extends through the secondary branch and spirals around the canal for electrically connecting the at least one electrode to the device.

2. The system according to claim 1, wherein the canal extends beyond the bifurcation.

3. The system according to claim 1, wherein the canal is closable.

4. The system according to claim 1, wherein the canal is closable by a blocking material injectable in the aperture.

5. The system according to claim 1, wherein the canal is closable by a plug installable in the aperture.

6. The system according to claim 1, wherein the primary branch is configured for being ligatured for closing the aperture.

7. The system according to claim 1, wherein a distance between a proximal end of the secondary branch and the bifurcation is substantially larger than a distance between the proximal end of the primary branch and the bifurcation.

8. The system according to claim 1, wherein the device is attachable to an implantable box.

9. The system according to claim 8, wherein the box comprises an electrical connector for releasably electrically co-operating with a further electrical connector situated at a proximal end of the secondary branch.

10. The system according to claim 1 further comprising the guide wire.

11. The system according to claim 1, wherein the primary branch is maintained as a straight cylinder while being guided into the brain tissue.

12. The system according to claim 1, wherein the probe is configured to conform to the brain tissue's geometry after removing the guide wire.

13. The system according to claim 1, wherein the probe is sufficiently flexible and/or bendable to prevent damage to the brain tissue after the guide wire's removal.

* * * * *